US012372449B1

United States Patent
Yang et al.

(10) Patent No.: US 12,372,449 B1
(45) Date of Patent: Jul. 29, 2025

(54) EXPERIMENTAL APPARATUS AND METHOD FOR SHALE SUPERCRITICAL SYNERGISTIC PENETRATION AND IMBIBITION BASED ON DAMPING VIBRATION

(71) Applicant: CHINA UNIVERSITY OF MINING AND TECHNOLOGY, BEIJING, Beijing (CN)

(72) Inventors: Liu Yang, Beijing (CN); Zhehan Yu, Beijing (CN); Long Tan, Beijing (CN); Jing Zhang, Beijing (CN); Yingwei Wang, Beijing (CN); Jianhua Qin, Beijing (CN)

(73) Assignee: CHINA UNIVERSITY OF MINING AND TECHNOLOGY, BEIJING, Beijing (CN)

( * ) Notice: Subject to any disclaimer, the term of this patent is extended or adjusted under 35 U.S.C. 154(b) by 0 days.

(21) Appl. No.: 19/015,779

(22) Filed: Jan. 10, 2025

(30) Foreign Application Priority Data

Jan. 12, 2024   (CN) .......................... 202410044835.0

(51) Int. Cl.
  *G01N 5/02*   (2006.01)
  *G01N 5/04*   (2006.01)
  (Continued)

(52) U.S. Cl.
  CPC ........... *G01N 5/04* (2013.01); *G01N 15/0806* (2013.01); *G01N 15/088* (2013.01); *G01N 33/24* (2013.01)

(58) Field of Classification Search
  CPC ......... G01N 5/00–04; G01N 13/00–04; G01N 15/00; G01N 15/08; G01N 15/0806; G01N 15/088; G01N 33/24
  See application file for complete search history.

(56) References Cited

U.S. PATENT DOCUMENTS

| 11,009,443 B2 * | 5/2021 | Guo ....................... G01N 33/24 |
| 11,092,586 B1 * | 8/2021 | Svarczkopf ........ G01N 15/0826 |

(Continued)

FOREIGN PATENT DOCUMENTS

| AU | 2021101771 A4 * | 5/2021 | ............... G01N 5/02 |
| AU | 2021102825 A4 * | 7/2021 | ............. G01N 13/00 |

(Continued)

OTHER PUBLICATIONS

CN-109507081-B Machine Translation (Year: 2021).*

(Continued)

*Primary Examiner* — Nguyen Q. Ha
(74) *Attorney, Agent, or Firm* — Bayramoglu Law Offices LLC

(57) ABSTRACT

The provided is an experimental apparatus and method for shale supercritical synergistic penetration and imbibition based on damping vibration, including a reaction autoclave; a damping vibration measurement device, used for measuring the weight of a rock sample; a temperature control device, used for heating and cooling the internal environment of the reaction autoclave; a pressure control device, disposed on the reaction autoclave lid; a water level control device, disposed on the upper inner wall of the reaction autoclave body; a conductivity testing device, disposed on the inner bottom of the reaction autoclave body; and a data processing device, disposed on the reaction autoclave body, used for receiving and processing signals transmitted from the damping vibration measurement device, temperature control device, pressure control device, water level control device, and conductivity testing device.

20 Claims, 6 Drawing Sheets

(51) Int. Cl.
*G01N 13/04* (2006.01)
*G01N 15/08* (2006.01)
*G01N 33/24* (2006.01)

(56) References Cited

U.S. PATENT DOCUMENTS

| | | | |
|---|---|---|---|
| 2012/0151998 A1* | 6/2012 | Willberg | G01N 13/00 73/38 |
| 2022/0390342 A1 | 12/2022 | Li et al. | |

FOREIGN PATENT DOCUMENTS

| | | | | |
|---|---|---|---|---|
| BE | 839527 | A | 9/1976 | |
| CN | 102778554 | A | 11/2012 | |
| CN | 106525687 | A | 3/2017 | |
| CN | 110969920 | A | 4/2020 | |
| CN | 111537697 | A | 8/2020 | |
| CN | 109507081 | B * | 1/2021 | G01N 15/08 |
| CN | 112459760 | A | 3/2021 | |
| CN | 113670778 | A * | 11/2021 | G01N 3/04 |
| CN | 214752499 | U | 11/2021 | |
| CN | 114486682 | A * | 5/2022 | G01N 15/082 |

OTHER PUBLICATIONS

CN-114486682-A Machine Translation (Year: 2022).*
CN-113670778-A Machine Translation (Year: 2021).*
Jia Li-Min, et al., A method for measuring damping coefficient of gravity sensor, Transducer and Microsystem Technologies, 2015, pp. 134-137, vol. 34 No. 12.

* cited by examiner

EXPERIMENTAL APPARATUS AND METHOD FOR SHALE SUPERCRITICAL SYNERGISTIC PENETRATION AND IMBIBITION BASED ON DAMPING VIBRATION

CROSS-REFERENCE TO THE RELATED APPLICATIONS

This application is based upon and claims priority to Chinese Patent Application No. 202410044835.0, filed on Jan. 12, 2024, the entire contents of which are incorporated herein by reference.

TECHNICAL FIELD

The present invention pertains to the technical field of shale oil resource development, and more specifically, it relates to an experimental apparatus and method for shale supercritical synergistic penetration and imbibition based on damping vibration.

BACKGROUND

Shale reservoirs are characterized by their tightness and the development of micro- and nano-scale pores, where capillary imbibition plays a significant role. Fully leveraging the spontaneous imbibition of massive hydraulic fracturing fluid to enhance oil recovery is crucial for improving the recovery rate of continental shale oil and accelerating exploration and development processes. Domestically and internationally, it has been proposed to inject supercritical $CO_2$ as a pre-energizing slug into shale formations before volumetric fracturing. This approach not only enhances rock fracturing and fracture formation but also replenishes formation energy and improves the properties of both shale and crude oil. This has gradually evolved into a "pre-$CO_2$ energized fracturing and displacement technology" that integrates fracturing, energizing, modification, and enhanced recovery. The pre-injected $CO_2$ interacts strongly with the shale/oil system, which can alter the pore structure, wettability, pressure distribution, oil storage state, and oil properties, thus complicating post-fracturing imbibition processes. The microscopic oil displacement mechanisms are still unclear, and there is no consensus regarding well shut-in applicability, shut-in times, and subsequent production methods.

Under subsurface conditions, $CO_2$ enters a supercritical state when the temperature reaches 31° C. and the pressure reaches 7.3 MPa. To better simulate the patterns of supercritical $CO_2$ synergistic penetration and imbibition, it is necessary to monitor the mass change of shale samples immersed in carbonated water in real time under high temperature and high pressure conditions, and to observe the precipitation, migration, and coalescence of oil-water-$CO_2$ bubbles. However, existing high-temperature, high-pressure imbibition experiments require removing samples at intervals to measure mass changes, thereby altering the original high-temperature, high-pressure formation environment. Moreover, high-temperature, high-pressure imbibition vessels primarily employ volumetric measurement methods, and the limited accuracy of volume metering burettes makes them unsuitable for shale reservoir samples with extremely low imbibition rates.

The present application provides an experimental apparatus and method for shale supercritical synergistic penetration and imbibition based on damping vibration, which enables the determination of sample vibration frequency under high temperature and high pressure conditions, thereby obtaining real-time measurements of sample mass change.

SUMMARY

Accordingly, the present invention provides an experimental apparatus and method for shale supercritical synergistic penetration and imbibition based on damping vibration, to address the problem in the prior art where the high-temperature, high-pressure conditions of the original formation are altered due to the need to remove samples at intervals to measure sample mass changes during experiments.

To achieve the aforementioned objectives, the present invention provides the following technical solutions:

According to a first aspect of the present invention, there is provided an experimental apparatus for shale supercritical synergistic penetration and imbibition based on damping vibration, comprising:

A reaction autoclave, including a reaction autoclave body and a reaction autoclave lid, wherein the reaction autoclave lid is disposed on the reaction autoclave body;

A damping vibration measurement device, including a first spring, an extendable sample clamp, a magnetic rod, a pressure-sensitive sensor, a second spring, a solenoid coil, an electromagnet, a dual control switch, and an ammeter;

Wherein the upper end of the first spring is connected to the reaction autoclave lid, the extendable sample clamp is connected to the lower end of the first spring, the magnetic rod is disposed on the extendable sample clamp, the pressure-sensitive sensor is mounted on the bottom inside the reaction autoclave body, the magnetic rod and the pressure-sensitive sensor are connected by the second spring, the solenoid coil and the electromagnet are mounted inside the reaction autoclave body and are connected to the two stages of the dual control switch respectively, the electromagnet is connected to a power source via the dual control switch, the solenoid coil is connected to the power source via the dual control switch, and the solenoid coil is signal connected to the ammeter;

A data processing device, disposed on the reaction autoclave body, for receiving the induced current generated by the magnetic rod oscillating up and down and continuously cutting the magnetic field lines within the solenoid coil.

Further, the apparatus also includes a temperature control device, a pressure control device, a water level control device, and a conductivity testing device, wherein the temperature control device includes a thermometer, a heating rod, and a liquid nitrogen circulation refrigeration device, the heating rod is disposed on the inner wall of the reaction autoclave body, and the liquid nitrogen circulation refrigeration device and the thermometer are disposed on the outer wall of the reaction autoclave body;

The pressure control device is disposed on the reaction autoclave lid, the water level control device is disposed on the upper inner wall of the reaction autoclave body, and the conductivity testing device is disposed on the inner bottom of the reaction autoclave body.

Further, the apparatus also includes a supercritical $CO_2$ circulation device, the supercritical $CO_2$ circulation device includes a confining pressure pump, a circulation pump, a temperature controller, a temperature sensor, a heater, a cooler, and a natural cooler, the confining pressure pump is in communication with the interior of the reaction autoclave body, the confining pressure pump is equipped with a temperature controller, and the confining pressure pump is also equipped with two circulation pumps, the two circulation pumps are respectively connected to the heater and the cooler, a natural cooler is disposed between the heater and the cooler, and the heater, the cooler, and the natural cooler are equipped with temperature sensors.

Further, the apparatus also includes a liquid defoaming device, the liquid defoaming device includes a stirring rod and an ultrasonic defoamer, the stirring rod is disposed inside the reaction autoclave body for stirring the liquid inside the reaction autoclave body, and the ultrasonic defoamer is disposed inside the reaction autoclave body for eliminating bubbles inside the reaction autoclave body.

Further, the apparatus also includes a data acquisition device, the data acquisition device includes a filter, an outlet pressure sensor, a back pressure vessel, a back pressure pump, a gas-liquid separator, a beaker, a dryer, a flow pressure gauge, a gas chromatograph, and a data acquisition center, the filter is in communication with the interior of the reaction autoclave body, the outlet pressure sensor is disposed at the gas outlet of the filter, the filter is connected to a gas-liquid separator and a back pressure vessel respectively, the back pressure vessel is connected to the back pressure pump via a dryer, the liquid inside the filter enters the beaker through the gas-liquid separator, the gas inside the filter is analyzed and measured by the flow pressure gauge and gas chromatograph after passing through the gas-liquid separator, the dryer is disposed between the gas-liquid separator and the flow pressure gauge, and the data acquisition center is used to display the measurement results of gas and liquid.

Further, the reaction autoclave also includes an explosion-proof glass observation window and a magnetic glass wiper, the explosion-proof glass observation window is embedded on the reaction autoclave body, the magnetic glass wiper is magnetically attached to the explosion-proof glass observation window, and the reaction autoclave body is also provided with an injection/extraction port for extracting and injecting gas or liquid.

According to a second aspect of the present invention, there is provided a method for shale supercritical synergistic penetration and imbibition based on damping vibration, using the above-described experimental apparatus for shale supercritical synergistic penetration and imbibition based on damping vibration, comprising the following steps:

Step S1: Perform a pre-experiment to test whether each device is operating normally, and the readings are accurate;

Step S2: Before the experiment starts, dry the rock sample and measure the mass of the dried rock sample;

Step S3: Fix the rock sample on the extendable sample clamp 22;

Step S4: Inject liquid or gas into the reaction autoclave body, and monitor the temperature and pressure inside the reaction autoclave body in real time until it reaches the preset pressure and temperature;

Step S5: Measure the mass of the rock sample after immersion based on the damping vibration measurement device, and combine it with the mass of the dried rock sample to obtain the mass change value of the rock sample until the mass change value stabilizes.

Further, in the step S5, the specific process of measuring the mass of the rock sample after immersion by the damping vibration measurement device is as follows:

The dual control switch connects the power source and the electromagnet, after the electromagnet is energized, it pulls the magnetic rod down, driving the extendable sample clamp to move downwards, and the first spring is pulled downwards;

By adjusting the power supply voltage, observe the descending speed of the extendable sample clamp until the bottom of the magnetic rod touches the pressure-sensitive sensor;

The pressure-sensitive sensor captures the pressure of the magnetic rod, triggers the dual control switch to disconnect the power source and the electromagnet, and connects the solenoid coil, the power source, and the ammeter;

Based on the electromagnet being de-energized, under the restoring force of the first spring, the extendable sample clamp and the magnetic rod are pulled upwards, the magnetic rod oscillates up and down and continuously cuts the magnetic field lines within the solenoid coil;

Based on the ammeter monitoring in real time the induced current generated by cutting the magnetic field lines, capturing the electrical signal, obtaining the vibration frequency of the magnetic rod, and combining it with the gas pressure inside the reaction autoclave body, calculating the mass of the rock sample after immersion.

Further, based on the vibration frequency of the magnetic rod, calculate the mass of the rock sample after immersion according to the first formula, wherein the first formula is:

$$m = \frac{k}{4\pi^2 f^2} - \alpha P;$$

Where m is the mass of the rock sample after immersion, f is the vibration frequency of the magnetic rod, k is the stiffness coefficient of the first spring, $\alpha$ is the added mass coefficient, and P is the gas pressure inside the reaction autoclave body.

Further, the method also includes the analysis of changes in the internal pore structure of the rock sample, specifically including:

Obtaining the porosity of the rock sample before the experiment, $P=\{P_1, P_2, P_3, P_4\}$, where $P_1$ is the microporosity of the rock sample before the experiment, $P_2$ is the small porosity of the rock sample before the experiment, $P_3$ is the mesoporosity of the rock sample before the experiment, and $P_4$ is the macroporosity of the rock sample before the experiment;

Obtaining the porosity of the rock sample after the experiment, $P'=\{P_1', P_2', P_3', P_4'\}$, where $P_1'$ is the microporosity of the rock sample before the experiment, $P_2'$ is the small porosity of the rock sample before the experiment, $P_3'$ is the mesoporosity of the rock sample before the experiment, and $P_4'$ is the macroporosity of the rock sample before the experiment;

Based on the porosity of the rock sample before the experiment and the porosity of the rock sample after the experiment, obtaining the porosity change rate $k=\{k_1, k_2, k_3, k_4\}$, where $k_1$ is the change rate of microporosity, $k_2$ is the change rate of small porosity, $k_3$ is the change rate of mesoporosity, and $k_4$ is the change rate of macroporosity;

Determining the formula for the dissolved volume of rock sample pores as:

$$\begin{cases} m_f = \rho v k \\ k = \dfrac{P' - P}{P} \end{cases} ;$$

Where $m_r$ is the dissolved volume of the rock sample pores, $\rho$ is the density of the rock sample, $v$ is the volume of the rock sample, $k$ is the porosity change rate of the rock sample, $P$ is the porosity of the rock sample before the experiment, and $P'$ is the porosity of the rock sample after the experiment.

The present invention has the following advantages:

The reaction autoclave provided in this application is equipped with a damping vibration measurement device for measuring the weight of the rock sample; a temperature control device for heating and cooling the internal environment of the reaction autoclave; a pressure control device, disposed on the reaction autoclave lid; a water level control device, disposed on the upper inner wall of the reaction autoclave body; a conductivity testing device, disposed on the inner bottom of the reaction autoclave body; and a data processing device, disposed on the reaction autoclave body, for receiving and processing the signals transmitted by the damping vibration measurement device, the temperature control device, the pressure control device, the water level control device, and the conductivity testing device.

The damping vibration measurement device provided in this application can perform real-time measurements, can measure under high temperature and high pressure conditions, and can measure in both liquid and gas. It can be combined with conventional high-temperature, high-pressure reaction autoclaves to monitor the mass change of rock samples within a high-temperature, high-pressure closed environment, which significantly improves testing accuracy and reduces labor costs.

BRIEF DESCRIPTION OF THE DRAWINGS

In order to more clearly illustrate the embodiments of the present invention or the technical solutions in the prior art, the accompanying drawings that need to be used in the embodiments or the prior art description will be briefly introduced below. It is evident that the accompanying drawings in the following description are merely exemplary. For those skilled in the art, other implementation drawings can also be derived from the provided drawings without any creative work.

The structures, proportions, sizes, etc., depicted in this specification are only used to complement the content disclosed in the specification, for the understanding and reading of those familiar with this technology, and are not intended to limit the limiting conditions that can be implemented by the present invention. Therefore, they do not have substantial technical significance. Any modifications to the structure, changes in proportional relationships, or adjustments in size, which do not affect the effectiveness and objectives that can be achieved by the present invention, shall still fall within the scope of the technical content disclosed by the present invention.

In the figures:
1 Reaction autoclave; 11 Reaction autoclave body; 12 Reaction autoclave lid; 13 Explosion-proof glass observation window; 14 Magnetic glass wiper; 15 Injection/extraction port; 2 Damping vibration measurement device; 21 First spring; 22 Extendable sample clamp; 23 Magnetic rod; 24 Pressure-sensitive sensor; 25 Second spring; 26 Solenoid coil; 27 Electromagnet; 3 Temperature control device; 31 Thermometer; 32 Heating rod; 33 Liquid nitrogen circulation refrigeration device; 4 Pressure control device; 5 Water level control device; 6 Conductivity testing device; 7 Data processing device; 8 Supercritical $CO_2$ circulation device; 81 Confining pressure pump; 82 Circulation pump; 83 Temperature controller; 84 Temperature sensor; 85 Heater; 86 Cooler; 87 Natural cooler; 9 Liquid defoaming device; 91 Stirring rod; 92 Ultrasonic defoamer; 10 Data acquisition device; 101 Filter; 102 Outlet pressure sensor; 103 Back pressure vessel; 104 Back pressure pump; 105 Gas-liquid separator; 106 Beaker; 107 Dryer; 108 Flow pressure gauge; 109 Gas chromatograph; 1010 Data acquisition center.

DETAILED DESCRIPTION OF THE EMBODIMENTS

The following specific embodiments are used to illustrate the implementation of the present invention. Those skilled in the art can easily understand other advantages and effects of the present invention from the content disclosed in this specification. Obviously, the described embodiments are part of the embodiments of the present invention, but not all of the embodiments. All other embodiments that a person of ordinary skill in the art could derive from the embodiments of the present invention without engaging in inventive activity are also within the scope of protection of the present invention.

Figure 1:
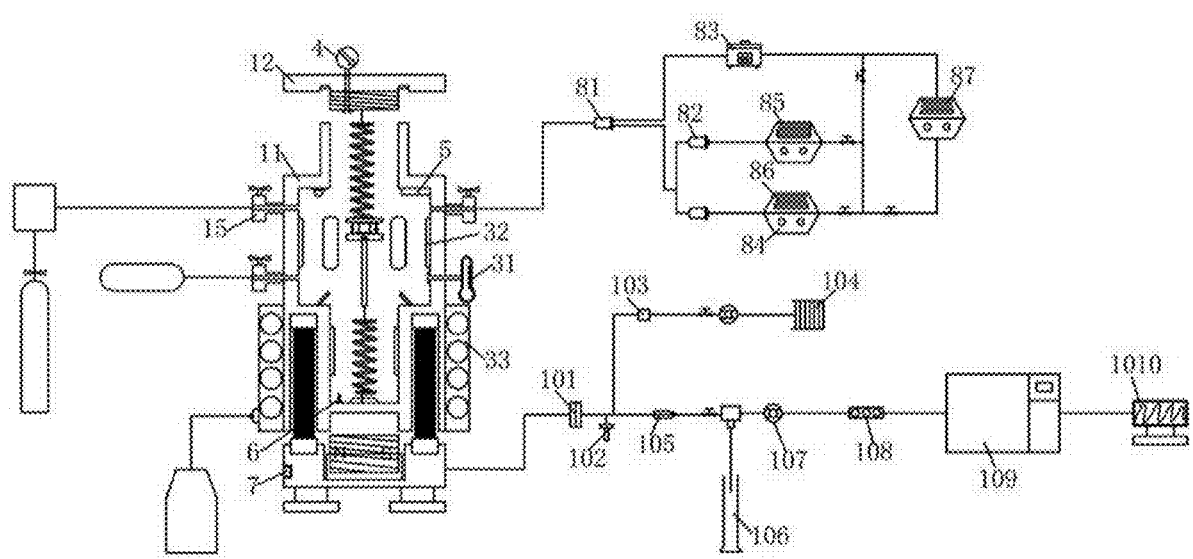
FIG. 1 is a schematic structural diagram of the shale supercritical synergistic penetration and imbibition experimental apparatus provided by the present invention.
Figure 2:
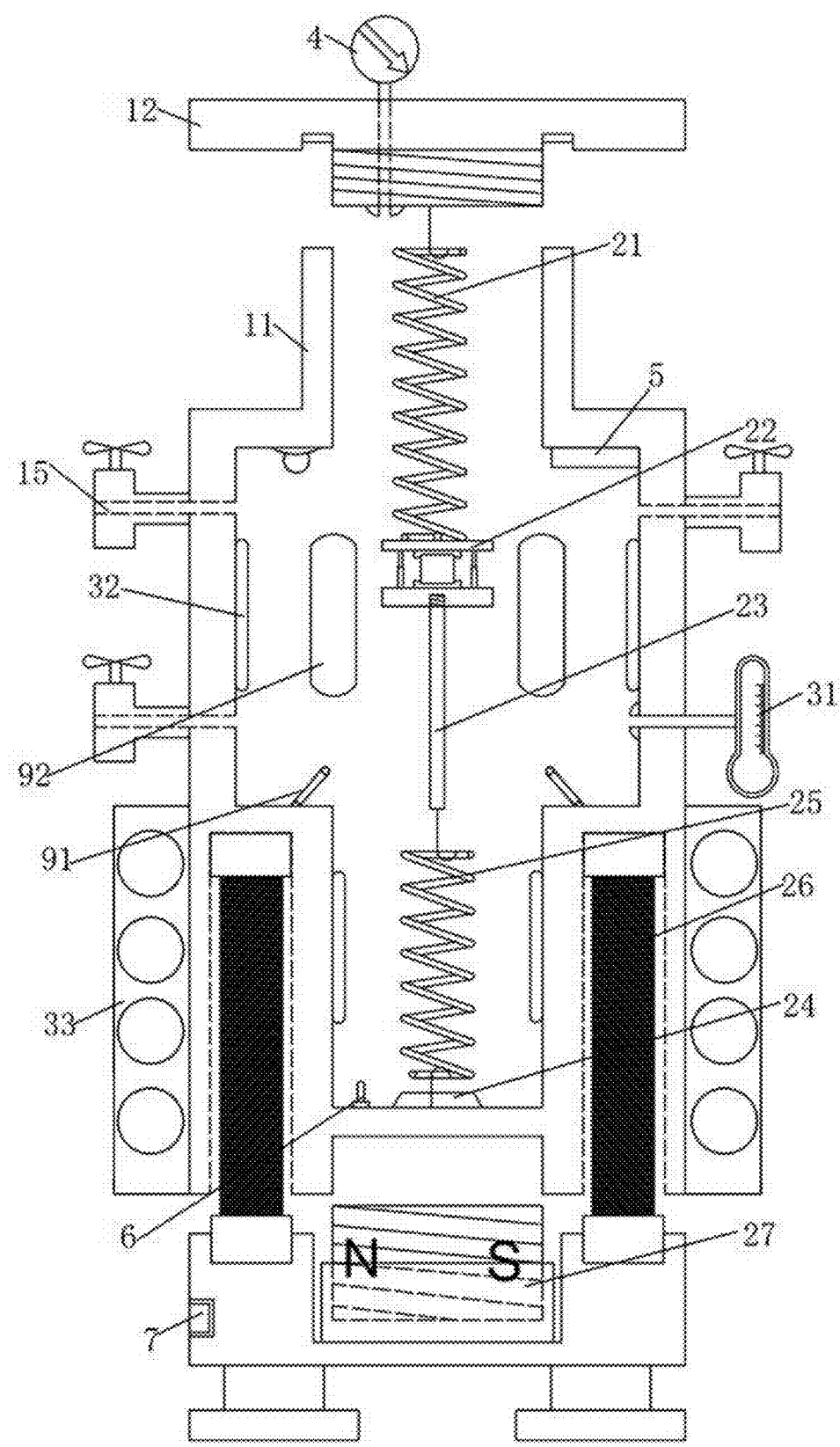
FIG. 2 is a schematic structural diagram of the reaction autoclave and the internal damping vibration measurement device provided by the experimental apparatus.
Figure 3:
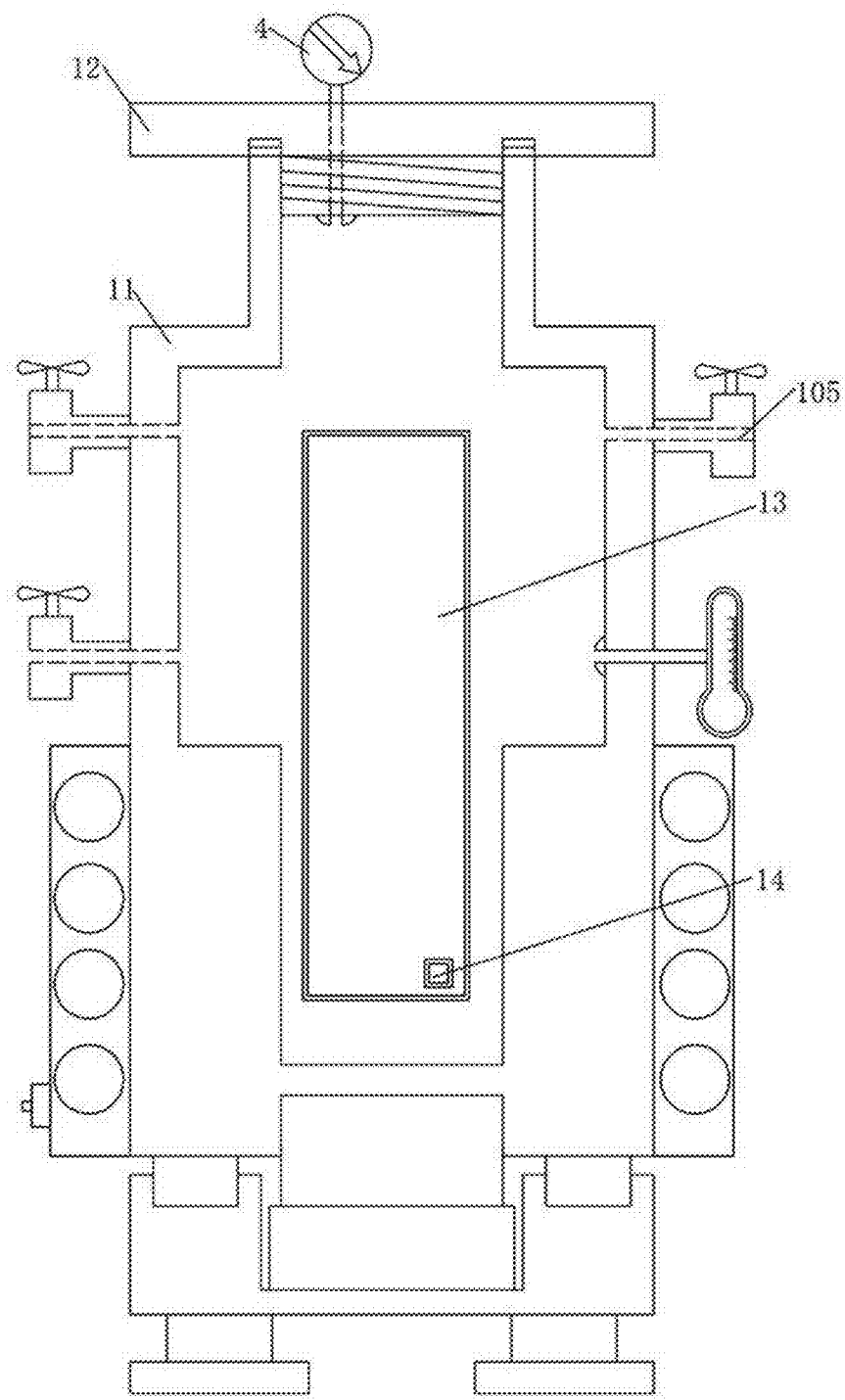
FIG. 3 is an external structural diagram of the reaction autoclave provided by the experimental apparatus.

According to a first aspect of the present invention, there is provided an experimental apparatus for shale supercritical synergistic penetration and imbibition based on damping vibration, as shown in FIGS. 1-3, comprising: a reaction autoclave 1, a damping vibration measurement device 2, a temperature control device 3, a pressure control device 4, a water level control device 5, a conductivity testing device 6, and a data processing device 7. The reaction autoclave 1 includes a reaction autoclave body 11, a reaction autoclave lid 12, an explosion-proof glass observation window 13, a magnetic glass wiper 14, and an injection/extraction port 15. The reaction autoclave body 11 and the reaction autoclave lid 12 are tightened by screwing clockwise and opened by unscrewing counterclockwise. The reaction autoclave lid 12 has a pressure sensor and a lamp. The lamp is used to illuminate the inside of the autoclave for easy observation.

The reaction autoclave body 11 is provided with an injection/extraction port 15, which can be used for gas or liquid extraction or injection. It has a sealing gasket and a flow control valve on its upper part, which can close or open the passage. The reaction autoclave body 11 is embedded with an explosion-proof glass observation window 13 to facilitate observation of the experimental situation inside the autoclave. The magnetic glass wiper 14 can be used to clean the glass when bubbles or water mist are generated.

The damping vibration measurement device 2 includes a first spring 21, an extendable sample clamp 22, a magnetic rod 23, a pressure-sensitive sensor 24, a second spring 25, a solenoid coil 26, an electromagnet 27, a dual control switch, and an ammeter. The upper end of the first spring 21 is connected to the reaction autoclave lid 12 through a hook, and the extendable sample clamp 22 is connected to the lower end of the first spring 21. The lower end of the extendable sample clamp 22 has a slot that can fit the magnetic rod 23, and the magnetic rod 23 is fixedly disposed on the extendable sample clamp 22. The extendable sample clamp 22 can be realized by using an extendable cylinder.

The pressure-sensitive sensor 24 is installed at the bottom inside the reaction autoclave body 11, and the magnetic rod 23 and the pressure-sensitive sensor 24 are connected by the second spring 25 and a hook. The solenoid coil 26 and the electromagnet 27 are installed inside the reaction autoclave body 11 and are connected to the two stages of the dual control switch, respectively. The electromagnet 27 is connected to a power source through the dual control switch, the solenoid coil 26 is connected to a power source through the dual control switch, and the solenoid coil 26 is signal connected to an ammeter.

The temperature control device 3 includes a thermometer 31, a heating rod 32, and a liquid nitrogen circulation refrigeration device 33. The heating rod 32 is disposed on the inner wall of the reaction autoclave body 11, and the liquid nitrogen circulation refrigeration device 33 and the thermometer 31 are disposed on the outer wall of the reaction autoclave body 11. The temperature of the reaction autoclave is controlled through the temperature control device 3, either by heating or cooling. The pressure control device 4 is a pressure sensor and is disposed on the reaction autoclave lid 12. The water level control device 5 is a water level alarm and is disposed on the upper inner wall of the reaction autoclave body 11. The conductivity testing device 6 is a conductivity tester and is disposed on the inner bottom of the reaction autoclave body 11. The data processing device 7 is disposed on the reaction autoclave body 11 and is used to receive and process the signals transmitted by the damping vibration measurement device 2, the temperature control device 3, the pressure control device 4, the water level control device 5, and the conductivity testing device 6.

The apparatus also includes a supercritical $CO_2$ circulation device 8. The supercritical $CO_2$ circulation device 8 includes a confining pressure pump 81, a circulation pump 82, a temperature controller 83, a temperature sensor 84, a heater 85, a cooler 86, and a natural cooler 87. The confining pressure pump 81 is used to maintain the pressure inside the reaction autoclave body 11, the circulation pump 82 is used to circulate the supercritical $CO_2$, the temperature controller 83 is used to control the temperature at the outlet of the $CO_2$ circulation device, the temperature sensor 84 is used to monitor the temperature information in real time, the heater 85 is used to heat the circulating supercritical $CO_2$, the cooler 86 is used to cool the circulating supercritical $CO_2$, and the natural cooler 87 is used to naturally cool the circulating supercritical $CO_2$.

The apparatus also includes a liquid defoaming device 9. The liquid defoaming device 9 includes a stirring rod 91 and an ultrasonic defoamer 92. The stirring rod 91 is disposed inside the reaction autoclave body 11 and is used to stir the liquid inside the reaction autoclave body 11. The ultrasonic defoamer 92 is disposed inside the reaction autoclave body 11 and is used to eliminate bubbles inside the reaction autoclave body 11.

The apparatus also includes a data acquisition device 10. The data acquisition device 10 includes a filter 101, an outlet pressure sensor 102, a back pressure vessel 103, a back pressure pump 104, a gas-liquid separator 105, a beaker 106, a dryer 107, a flow pressure gauge 108, a gas chromatograph 109, and a data acquisition center 1010. The back pressure pump 104 and the back pressure vessel 103 are used to reflux the liquid and gas after the experiment, the filter 101 is used to filter impurities in the liquid and gas, the outlet pressure sensor 102 is used to monitor the outlet pressure, the gas-liquid separator 105 is used to separate the gas and liquid, the beaker 106 is used to measure the liquid volume, the dryer 107 is used to dry the gas, the flow pressure gauge 108 is used to measure the flow pressure of the dried gas, the gas chromatograph 109 is used to analyze the gas composition, and the data acquisition center 1010 is used to display the measurement results of gas and liquid.

In this implementation method, first, the power supply and the computer should be connected to make the internal circuit of the device start working. When the light inside the autoclave is on, it indicates that the device is powered on. Open the device control software on the computer, and you can see the real-time readings of the temperature control device 3 and the pressure control device 4. Secondly, the rock sample should be placed into the reaction autoclave.

Specifically, first open the reaction autoclave lid 12, confirm that the inside is clean and free of foreign matter, and then fix the rock sample in the extendable sample clamp 22. More specifically, first remove the first spring 21, the extendable sample clamp 22, and the magnetic rod 23 from the hook on the reaction autoclave lid 12. Pull apart the extendable sample clamp 22 and clamp the rock sample in the rubber pads inside the clamp to prevent the clamp from damaging the rock sample. Insert the magnetic rod 23 into the installation slot at the bottom of the extendable sample clamp 22. There is a helical structure inside the installation slot, and there are threads on the upper end of the magnetic rod 23. The magnetic rod 23 can be installed and fixed at the bottom of the extendable sample clamp 22 by screwing clockwise. Connect the magnetic rod 23 and the pressure-sensitive sensor 24 with the second spring 25, then connect the extendable sample clamp 22 and the second spring 25 in a suspended manner, and finally hook the first spring 21 onto the hook of the reaction autoclave lid 12, and then close the reaction autoclave lid 12.

First, a pre-experiment should be performed to test whether each device is operating normally and the readings are accurate. Specifically, the rock sample is replaced with a standard test block. As described above, after installation and confirming that all injection/extraction ports 15 are closed, connect a water pipe to any one of the injection/extraction ports 15 for water injection. Fill the water level above the water level alarm and check whether the light changes from a steady yellow light to a flashing red light, and whether alarm information is received on the computer software.

Start the damping vibration measurement device 2 and click on the mass test on the computer software. At this time, the dual control switch connects the power source and the electromagnet 27 at the bottom of the autoclave. Due to the magnetic force after being powered on, the magnetic rod 23 is pulled down, driving the extendable sample clamp 22 to move downward. The first spring 21 is stretched accordingly. At this time, the power supply voltage should be manually adjusted slowly from low to high while observing the descending speed of the extendable sample clamp 22 inside the autoclave. Control the entire system to descend slowly until the bottom of the magnetic rod 23 touches the pressure-sensitive sensor 24 at the bottom of the autoclave. The pressure-sensitive sensor 24 can capture the sudden and extremely small increase in pressure, triggering the dual control switch to disconnect the connection between the power source and the electromagnet 27, and connect the solenoid coil 26 and the micro ammeter inside the autoclave body.

Specifically, when the electromagnet 27 is de-energized, the magnetic force disappears. Under the action of the first spring 21, the extendable sample clamp 22 and the magnetic rod 23 will be pulled upward, and then oscillate up and down inside the autoclave. The magnetic rod 23 continuously cuts the magnetic lines during the up and down oscillation, generating an induced current. The current is transmitted through the line to the micro ammeter for real-time readings, which is then processed by the processing chip and displayed on the data acquisition center 1010. Compare the mass of the first spring 21, the extendable sample clamp 22, the magnetic rod 23, and the standard block measured before the experiment to determine whether the damping vibration measurement device 2 is operating normally.

Next, perform the pressurization operation. Connect the air through an injection/extraction port 15 to the compressor. Select one of the remaining two injection/extraction ports 15 to connect a pressure gauge. Compare the pressure reading of the pressure monitoring system inside the autoclave with the pressure reading of the pressure gauge to determine whether the system is working properly. After releasing the pressure, open the lid and perform conductivity and temperature tests.

Specifically, enter the target temperature on the computer, and wait for the processing chip to turn on the heating rod 32 to heat to the target temperature. Use an external thermometer 31 to measure the temperature and compare the reading of the system inside the autoclave with the reading of the thermometer 31 to determine whether the temperature control system is working properly. Finally, test the conductivity. Click on the conductivity test, and command the input/output port to reach the processing chip, which starts the conductivity tester. Test the conductivity of the liquid inside the autoclave using a sinusoidal wave voltage with a frequency of 1-3 kHz. Then, process the readings through the processing chip and display them on the data acquisition center 1010. Use an external conductivity meter to test the conductivity of the liquid inside the autoclave, compare the two values, and determine whether the conductivity testing system is working properly.

Further, make sure all injection/extraction ports 15 are closed. Connect a vacuum pump to any one of the injection/extraction ports 15. In this embodiment, use the injection/extraction port 15 to evacuate the inside of the autoclave to a negative pressure state. Specifically, when a tube is inserted into the injection/extraction port 15, the sealing ring will tightly surround and seal the tube section. There is a knob on the outside of the injection/extraction port 15 that can control the speed of fluid or gas flowing in or out. More specifically, the injection/extraction port 15 is sealed by a sealing ring, and a flow control valve controls the flow rate of fluid or gas flowing in or out. When the vacuuming is completed, first close the injection/extraction port 15, and then pull out the tube.

Further, connect a water pipe to any one of the injection/extraction ports 15 for water injection. Specifically, before inserting the water pipe into the injection/extraction port 15, the air in the pipe should be purged first. First, open the water valve and use the water flow to purge the air. While closing the water valve, pinch the pipe with your hand and quickly insert the water pipe into the injection/extraction port 15. Open the flow control valve and observe through the explosion-proof glass observation window 13. Due to the internal negative pressure, the water will be sucked into the autoclave. Open the water valve and observe the water level inside the autoclave until it reaches the desired height. If the water level exceeds the water level alarm, the light will change from a yellow light to a flashing red light.

Furthermore, connect the $CO_2$ gas cylinder to any one of the injection/extraction ports 15. Specifically, if it is required that the pressure in the reaction autoclave 1 reach a relatively high level, a $CO_2$ gas cylinder can be connected to a pressure pump according to the need, and then connected to the injection/extraction port 15 for pressurization. When the pressurization is completed, first close the injection/extraction port 15, and then pull out the tube. During the injection of $CO_2$ or other gases and liquids, the stirring rod 91 can be started as required to stir the internal liquid and increase the contact area between the liquid and gas. The ultrasonic defoamer 92 can be started as needed to perform defoaming and degassing of the liquid and gas inside the autoclave through ultrasound.

After the injection of liquid and gas is completed, in order to ensure that the supercritical $CO_2$ in the autoclave can fully contact the rock sample and fully dissolve into the liquid, it is necessary to connect the supercritical $CO_2$ circulation device 8 through any one of the injection/extraction ports 15. Specifically, when the device is connected, start the confining pressure pump 81 to ensure that the pressure inside the autoclave remains unchanged, and then start the circulation pump 82 according to the required temperature change. More specifically, when heating is required, start the circulation pump 82 to draw the $CO_2$ inside the autoclave to the temperature sensor 84. At this time, the processing chip will, according to the target temperature input in the data acquisition center 1010, use the heater 85 to heat the $CO_2$ gas, and return it to the autoclave through the temperature controller 83 and the confining pressure pump 81. When cooling is required, start the circulation pump 82 to draw the $CO_2$ inside the autoclave to the temperature sensor 84. At this time, the processing chip will, according to the target temperature input in the data acquisition center 1010, use the cooler 86 to cool the $CO_2$ gas, and return it to the autoclave through the temperature controller 83 and the confining pressure pump 81. When natural cooling is required, start the circulation pump 82 to draw the $CO_2$ inside the autoclave to the temperature sensor 84. At this time, the processing chip will, according to the target temperature input in the data acquisition center 1010, use the natural cooler 87 to control the $CO_2$ gas to return to room temperature, and return it to the autoclave through the temperature controller 83 and the confining pressure pump 81.

During the above injection or removal of gas or liquid, the temperature sensor 84 and the pressure sensor monitor the temperature and pressure data inside the autoclave in real time. After processing by the processing chip, the data is transmitted and displayed on the data acquisition center 1010. During the above injection or removal of gas or liquid, the target pressure can be input in the data acquisition center 1010. When the system reaches this pressure, it will automatically close the flow valve. The temperature inside the autoclave can be controlled by the temperature control device 3 during or before/after the above operations. Specifically, by adjusting the target temperature on the data acquisition center 1010, the processing chip will automatically start the heating rod 32 to heat or the liquid nitrogen circulation device to cool, adjusting the temperature inside the autoclave to the target temperature±0.1° C., so as to achieve a precise high-temperature and high-pressure environment.

After the experiment, the liquid and gas in the autoclave are drawn into the data acquisition device 10 for residual liquid and gas after the experiment through the back pressure pump 104. First, the mixture passes through a filter 101 to filter out any possible rock debris or other impurities. Then, it passes through an outlet pressure sensor 102 to monitor its outlet pressure. Next, it passes through a gas-liquid separator 105 to separate the gas and liquid. The liquid enters a beaker 106 for volume measurement. The gas enters a dryer 107 for drying and then enters a high-precision flow pressure gauge 108 to measure flow pressure. After that, it enters a gas chromatograph 109 to analyze the gas composition, and finally, it is displayed on the data acquisition center 1010. The back pressure vessel 103 is used to prevent residual liquid from entering the back pressure pump 104. The residual liquid is dried in a dryer 107 and then discharged into the air or a gas recovery pipe.

Figure 4:
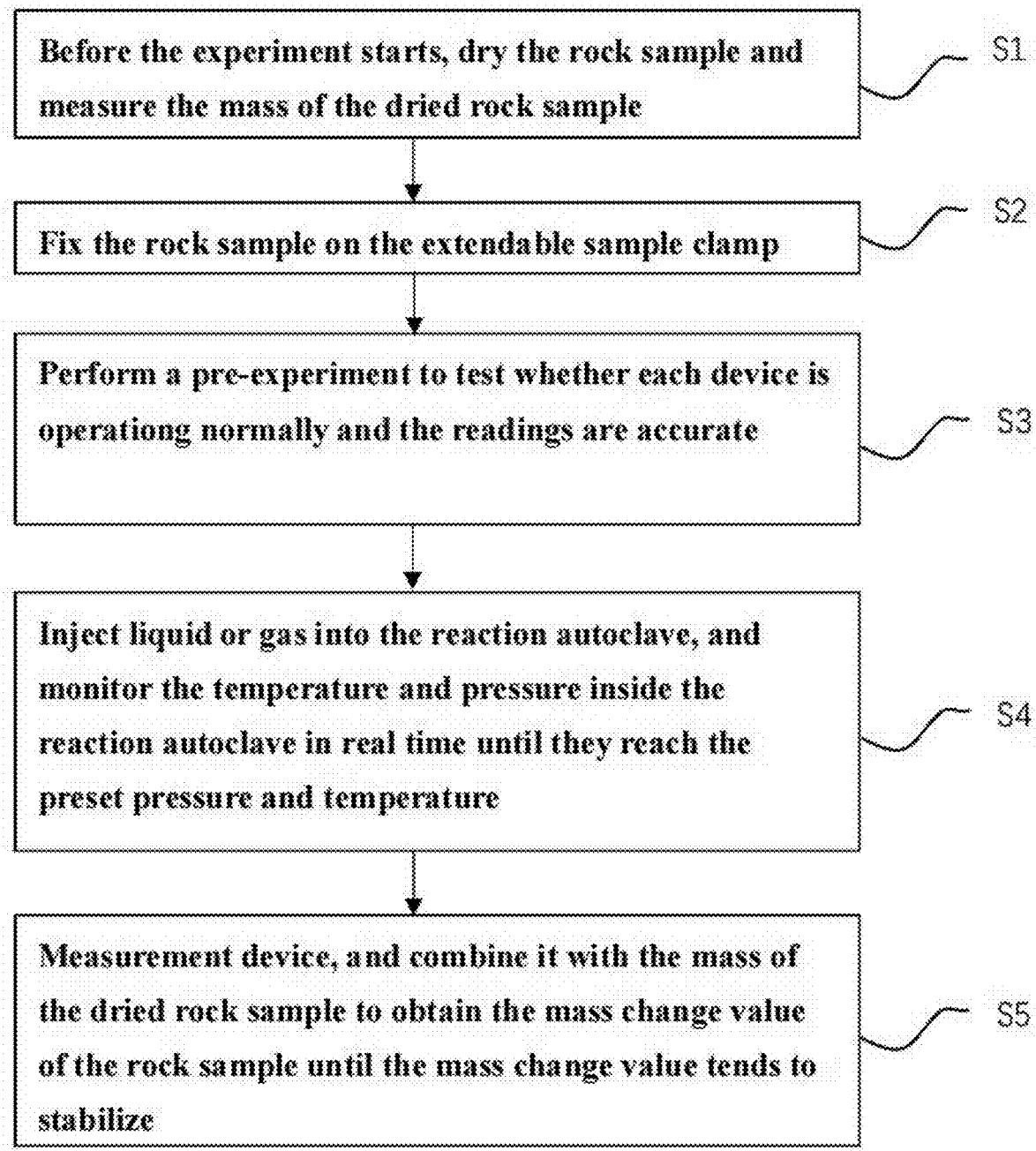
FIG. 4 is a flow chart of the shale supercritical synergistic penetration and imbibition experimental method provided by the present invention.

According to a second aspect of the present invention, there is provided a method for shale supercritical synergistic penetration and imbibition based on damping vibration, using the experimental apparatus for shale supercritical synergistic penetration and imbibition based on damping vibration. As shown in FIG. 4, the method includes the following steps:

Step S1: Perform a pre-experiment to test whether each device is operating normally, and the readings are accurate;

Step S2: Before the experiment starts, dry the rock sample and measure the mass of the dried rock sample;

Step S3: Fix the rock sample on the extendable sample clamp 22;

Step S4: Inject liquid or gas into the reaction autoclave body 11, and monitor the temperature and pressure inside the reaction autoclave body 11 in real time until it reaches the preset pressure and temperature;

Step S5: Measure the mass of the rock sample after immersion based on the damping vibration measurement device, and combine it with the mass of the dried rock sample to obtain the mass change value of the rock sample until the mass change value stabilizes.

In Step S5, the specific process of measuring the mass of the rock sample after immersion by the damping vibration measurement device 2 is as follows:

The dual control switch connects the power source and the electromagnet 27. After the electromagnet 27 is energized, it pulls the magnetic rod 23 down, driving the extendable sample clamp 22 to move downward, and the first spring 21 is pulled downward;

By adjusting the power supply voltage, observe the descending speed of the extendable sample clamp 22 until the bottom of the magnetic rod 23 touches the pressure-sensitive sensor 24;

The pressure-sensitive sensor 24 captures the pressure of the magnetic rod 23, triggering the dual control switch to disconnect the connection between the power source and the electromagnet 27, and connect the solenoid coil 26, the power source, and the ammeter;

Based on the electromagnet 27 being de-energized, under the restoring force of the first spring 21, the extendable sample clamp 22 and the magnetic rod 23 are pulled upward, the magnetic rod 23 oscillates up and down and continuously cuts the magnetic field lines within the solenoid coil 26;

Based on the ammeter monitoring in real time the induced current generated by cutting the magnetic field lines, capturing the electrical signal, obtaining the vibration frequency of the magnetic rod 23, and combining it with the gas pressure inside the reaction autoclave body, calculating the mass of the rock sample after immersion according to the first formula.

The first formula is:

$$m = \frac{k}{4\pi^2 f^2} - \alpha P;$$

Where m is the mass of the rock sample after immersion, f is the vibration frequency of the magnetic rod, k is the stiffness coefficient of the first spring, α is the added mass coefficient, and P is the gas pressure inside the reaction autoclave body.

The method also includes the analysis of changes in the internal pore structure of the rock sample, specifically including:

Obtaining the porosity of the rock sample before the experiment, $P=\{P_1, P_2, P_3, P_4\}$, where $P_1$ is the microporosity of the rock sample before the experiment, $P_2$ is the small porosity of the rock sample before the experiment, $P_3$ is the mesoporosity of the rock sample before the experiment, and $P_4$ is the macroporosity of the rock sample before the experiment;

Obtaining the porosity of the rock sample after the experiment, $P'=\{P_1', P_2', P_3', P_4'\}$, where $P_1'$ is the microporosity of the rock sample after the experiment, $P_2'$ is the small porosity of the rock sample after the experiment, $P_3'$ is the mesoporosity of the rock sample after the experiment, and $P_4'$ is the macroporosity of the rock sample after the experiment;

Based on the porosity of the rock sample before the experiment and the porosity of the rock sample after the experiment, obtaining the porosity change rate $k=\{k_1, k_2, k_3, k_4\}$, where $k_1$ is the change rate of microporosity, $k_2$ is the change rate of small porosity, $k_3$ is the change rate of mesoporosity, and $k_4$ is the change rate of macroporosity;

Determining the formula for the dissolved volume of rock sample pores as:

$$\begin{cases} m_r = \rho v k \\ k = \frac{P' - P}{P} \end{cases};$$

Where $m_r$ is the dissolved volume of the rock sample pores, ρ is the density of the rock sample, v is the volume of the rock sample, k is the porosity change rate of the rock sample, P is the porosity of the rock sample before the experiment, and P' is the porosity of the rock sample after the experiment.

Figure 5:
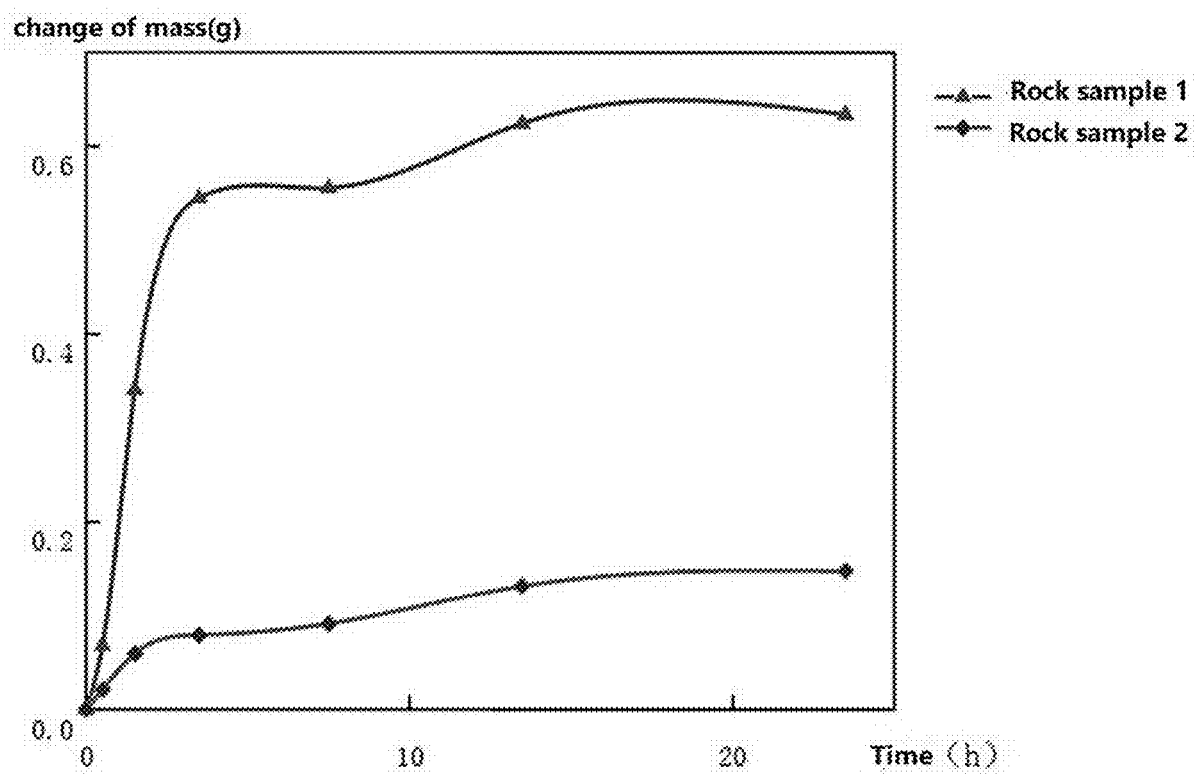
FIG. 5 is a mass change value-time graph of rock sample 1 and rock sample 2 in the embodiment provided by the present invention.

In the experiment, we selected a spring stiffness coefficient k=1800, a gas pressure inside the autoclave of P=1500 psig, an added mass coefficient α=0.0011, and selected two rock samples with masses of $m_1$=27.9110 g and $m_2$=29.1327 g, respectively, weighed on a high-precision electronic balance, to perform two experiments. The experimental results are shown in FIG. 5, where the mass change values gradually stabilize.

When liquid or gas permeates into or out of the rock sample, and pores are filled or emptied, the mass will change. Based on the change in mass, it can be determined whether the rock sample has reached saturation or whether the original oil stored internally has been expelled.

Figure 6B:
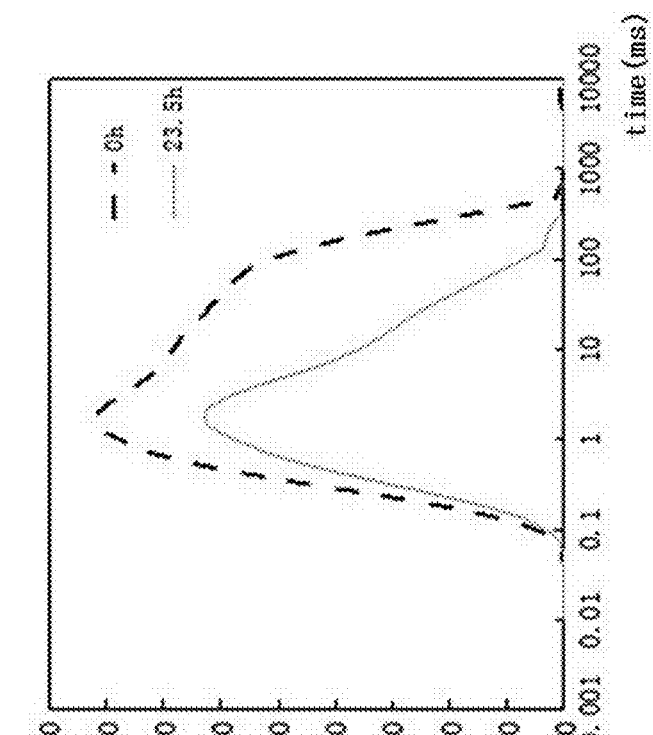
FIGS. 6A and 6B show a nuclear magnetic resonance $T_2$ spectrum of rock sample 1 and rock sample 2 in the embodiment provided by the present invention.
Figure 6A:
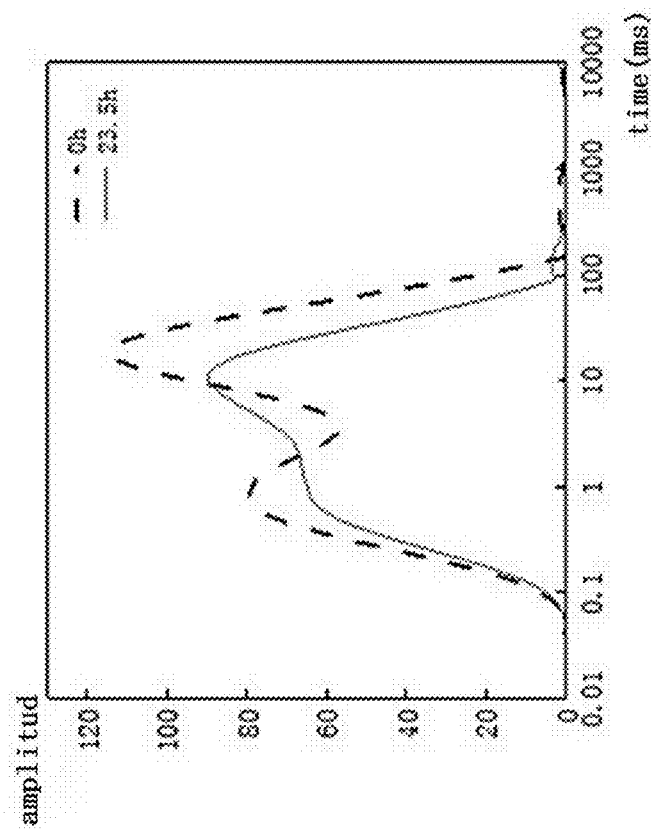

The determination method is as follows:

The recovery rate can be calculated by the change rate of the area of the curve amplitude, as shown in FIGS. 6A and 6B. Let the curve function be $f(t)$, and the recovery rate formula is:

$$ER = \frac{\int_0^{x_2} f(t)dt - \int_0^{x_1} f(t)dt}{\int_0^{x_1} f(t)dt};$$

Where $x_1$ is the amplitude at time 0 h, and $x_2$ is the amplitude at time 23.5 h.

The recovery rate on the left side of the figure is ER=19.58%, and the recovery rate on the right side of the figure is ER=45.91%. Based on the change in the nuclear magnetic resonance (NMR) spectrum area and the porosity data, the volume of oil discharged from inside the rock sample can be calculated. The volume of oil discharged is equal to the volume of water absorbed, thereby obtaining the mass of oil discharged and the mass of water absorbed by the rock sample.

Based on the mass of the rock sample after oil discharge and water absorption, as measured by the damping vibration measurement device, and based on the mass of the rock sample before the experiment, the mass change value of the rock sample is obtained. By comparing the obtained mass of oil discharged and water absorbed with the mass change value, it can be determined whether the rock sample has reached saturation or whether the original oil stored internally has been expelled.

During the experiment, the rock sample will imbibe supercritical $CO_2$. Under the action of $CO_2$, significant changes in the pore structure will occur inside the rock sample, with a decrease in the number of small pores and an increase in the number of medium and large pores. When the NMR relaxation time is <1 ms, it is considered as micropores; 1-10 ms, small pores; 10-100 ms, mesopores; and >100 ms, macropores.

As shown in FIG. 6A, the recovery rate in the micropore region <1 ms is 20.68%, the recovery rate in the small pore region of 1-10 ms is 7.64%, the recovery rate in the mesopore region of 10-100 ms is 39.98%, and the recovery rate in the macropore region >100 ms is 57.85%. The micropore recovery rate is slightly higher than the total recovery rate of 19.58%, indicating that micropores are not easily corroded by carbonic acid. The small pore recovery rate is much lower than the total recovery rate, while the mesopore and macropore recovery rates are much higher than the total recovery rate, indicating that mesopores and macropores are more easily corroded by carbonic acid, and that small pores are easily corroded by carbonic acid into mesopores and macropores.

Taking the experimental rock sample on FIG. 6A as an example, its porosity measured before the experiment was 7.03%, its volume was 24.53 cm$^3$, and its density was 2.2 g/cm$^3$. After the experiment, its porosity was 7.57%, and the porosity change rate k=0.77%. It was calculated that the rock sample was dissolved by 0.4155 g.

Although the present invention has been described in detail above with general descriptions and specific embodiments, some modifications or improvements can be made to it based on the present invention, which is obvious to those skilled in the art. Therefore, such modifications or improvements made without departing from the spirit of the present invention shall all fall within the scope of protection requested by the present invention.

What is claimed is:

1. An experimental apparatus for shale supercritical synergistic penetration and imbibition based on damping vibration, comprising:
   a reaction autoclave, comprising a reaction autoclave body and a reaction autoclave lid, wherein the reaction autoclave lid is disposed on the reaction autoclave body;
   a damping vibration measurement device, comprising a first spring, an extendable sample clamp, a magnetic rod, a pressure-sensitive sensor, a second spring, a solenoid coil, an electromagnet, a dual control switch, and an ammeter;
   wherein an upper end of the first spring is connected to the reaction autoclave lid, the extendable sample clamp is connected to a lower end of the first spring, the magnetic rod is disposed on the extendable sample clamp, the pressure-sensitive sensor is mounted on a bottom inside the reaction autoclave body, the magnetic rod and the pressure-sensitive sensor are connected by the second spring, the solenoid coil and the electromagnet are mounted inside the reaction autoclave body and are connected to two poles of the dual control switch respectively, the electromagnet is connected to a power source via the dual control switch, the solenoid coil is connected to a power source via the dual control switch, and the solenoid coil is signal connected to the ammeter;
   a data processing device, disposed on the reaction autoclave body, for receiving an induced current generated by the magnetic rod oscillating up and down and continuously cutting magnetic field lines within the solenoid coil.

2. The experimental apparatus for the shale supercritical synergistic penetration and imbibition based on the damping vibration according to claim 1, further comprising a temperature control device, a pressure control device, a water level control device, and a conductivity testing device, wherein the temperature control device comprises a thermometer, a heating rod, and a liquid nitrogen circulation refrigeration device, the heating rod is disposed on an inner wall of the reaction autoclave body, and the liquid nitrogen circulation refrigeration device and the thermometer are disposed on an outer wall of the reaction autoclave body;
   the pressure control device is disposed on the reaction autoclave lid, the water level control device is disposed on an upper inner wall of the reaction autoclave body, and the conductivity testing device is disposed on an inner bottom of the reaction autoclave body.

3. The experimental apparatus for the shale supercritical synergistic penetration and imbibition based on the damping vibration according to claim 1, further comprising a supercritical $CO_2$ circulation device, the supercritical $CO_2$ circulation device comprises a confining pressure pump, a circulation pump, a temperature controller, a temperature sensor, a heater, a cooler, and a natural cooler, the confining pressure pump is in communication with an interior of the reaction autoclave body, the confining pressure pump is provided with the temperature controller, and the confining pressure pump is further provided with two circulation pumps, the two circulation pumps are respectively connected to the heater and the cooler, a natural cooler is provided between the heater and the cooler, and the heater, the cooler, and the natural cooler are provided with temperature sensors.

4. The experimental apparatus for the shale supercritical synergistic penetration and imbibition based on the damping vibration according to claim 1, further comprising a liquid defoaming device, the liquid defoaming device comprises a stirring rod and an ultrasonic defoamer, the stirring rod is disposed inside the reaction autoclave body for stirring a liquid inside the reaction autoclave body, and the ultrasonic defoamer is disposed inside the reaction autoclave body for eliminating bubbles inside the reaction autoclave body.

5. The experimental apparatus for the shale supercritical synergistic penetration and imbibition based on the damping vibration according to claim 1, further comprising a data acquisition device, the data acquisition device comprises a filter, an outlet pressure sensor, a back pressure vessel, a back pressure pump, a gas-liquid separator, a beaker, a dryer, a flow pressure gauge, a gas chromatograph, and a data acquisition center, the filter is in communication with an interior of the reaction autoclave body, the outlet pressure sensor is disposed at a gas outlet of the filter, the filter is connected to the gas-liquid separator and the back pressure vessel respectively, the back pressure vessel is connected to the back pressure pump via the dryer, a liquid inside the filter enters the beaker through the gas-liquid separator, a gas inside the filter is analyzed and measured by the flow pressure gauge and the gas chromatograph after passing through the gas-liquid separator, the dryer is disposed between the gas-liquid separator and the flow pressure gauge, and the data acquisition center is configured to display measurement results of gas and liquid.

6. The experimental apparatus for the shale supercritical synergistic penetration and imbibition based on the damping vibration according to claim 1, wherein the reaction autoclave further comprises an explosion-proof glass observation window and a magnetic glass wiper, the explosion-proof glass observation window is embedded on the reaction autoclave body, the magnetic glass wiper is magnetically attached to the explosion-proof glass observation window, and the reaction autoclave body is further provided with an injection/extraction port for extracting and injecting gas or liquid.

7. A method for shale supercritical synergistic penetration and imbibition based on damping vibration, using the experimental apparatus for the shale supercritical synergistic penetration and imbibition based on the damping vibration according to claim 1, comprising the following steps:
  step S1: performing a pre-experiment to test whether each device is operating normally, and the readings are accurate;
  step S2: before the experiment starts, drying the rock sample and measure the mass of the dried rock sample;
  step S3: fixing the rock sample on the extendable sample clamp;
  step S4: injecting liquid or gas into the reaction autoclave body, and monitoring temperature and pressure inside the reaction autoclave body in real time until reaching preset pressure and temperature;
  step S5: measuring the mass of the rock sample after immersion based on the damping vibration measurement device, and combining the mass of the rock sample after immersion with the mass of the dried rock sample to obtain a mass change value of the rock sample until the mass change value stabilizes.

8. The method for the shale supercritical synergistic penetration and imbibition based on the damping vibration according to claim 7, wherein in the step S5, a process of measuring the mass of the rock sample after immersion by the damping vibration measurement device is as follows:
  the dual control switch connects the power source and the electromagnet, after the electromagnet is energized, the electromagnet pulls the magnetic rod down, driving the extendable sample clamp to move downwards, and the first spring is pulled downwards;
  by adjusting a power supply voltage, a descending speed of the extendable sample clamp is observed until a bottom of the magnetic rod touches the pressure-sensitive sensor;
  the pressure-sensitive sensor captures a pressure of the magnetic rod, triggers the dual control switch to disconnect a connection between the power source and the electromagnet, and connect the solenoid coil, the power source, and the ammeter;
  based on the electromagnet being de-energized, under a restoring force of the first spring, the extendable sample clamp and the magnetic rod are pulled upwards, the magnetic rod oscillates up and down and continuously cuts the magnetic field lines within the solenoid coil;
  based on the ammeter monitoring in real time the induced current generated by cutting the magnetic field lines, an electrical signal is captured, a vibration frequency of the magnetic rod is obtained, and the vibration frequency of the magnetic rod is combined with a gas pressure inside the reaction autoclave body, the mass of the rock sample after immersion is calculated.

9. The method for the shale supercritical synergistic penetration and imbibition based on the damping vibration according to claim 8, wherein based on the vibration frequency of the magnetic rod, the mass of the rock sample after immersion is calculated according to a first formula, the first formula being:

$$m = \frac{k}{4\pi^2 f^2} - \alpha P;$$

wherein m is the mass of the rock sample after immersion, f is the vibration frequency of the magnetic rod, k is a stiffness coefficient of the first spring, $\alpha$ is an added mass coefficient, and P is the gas pressure inside the reaction autoclave body.

10. The method for the shale supercritical synergistic penetration and imbibition based on the damping vibration according to claim 7, further comprising an analysis of changes in an internal pore structure of the rock sample, comprising:
  a porosity of the rock sample before the experiment, $P=\{P_1, P_2, P_3, P_4\}$, wherein $P_1$ is a microporosity of the rock sample before the experiment, $P_2$ is a small porosity of the rock sample before the experiment, $P_3$ is a mesoporosity of the rock sample before the experiment, and $P_4$ is a macroporosity of the rock sample before the experiment;

obtaining a porosity of the rock sample after the experiment, P'={P$_1$', P$_2$', P$_3$', P$_4$'}, wherein P$_1$' is a microporosity of the rock sample after the experiment, P$_2$' is a small porosity of the rock sample after the experiment, P$_3$' is a mesoporosity of the rock sample after the experiment, and P$_4$' is a macroporosity of the rock sample after the experiment;

based on the porosity of the rock sample before the experiment and the porosity of the rock sample after the experiment, obtaining a porosity change rate k={k$_1$, k$_2$, k$_3$, k$_4$}, wherein k$_1$ is a change rate of microporosity, k$_2$ is a change rate of small porosity, k$_3$ is a change rate of mesoporosity, and k$_4$ is a change rate of macroporosity;

determining a formula for a dissolved volume of rock sample pores as:

$$\begin{cases} m_r = \rho v k \\ k = \dfrac{P' - P}{P} \end{cases} ;$$

wherein m$_r$ is the dissolved volume of the rock sample pores, ρ is a density of the rock sample, v is a volume of the rock sample, k is the porosity change rate of the rock sample, P is the porosity of the rock sample before the experiment, and P' is the porosity of the rock sample after the experiment.

11. The method according to claim 7, wherein the experimental apparatus further comprises a temperature control device, a pressure control device, a water level control device, and a conductivity testing device, wherein the temperature control device comprises a thermometer, a heating rod, and a liquid nitrogen circulation refrigeration device, the heating rod is disposed on an inner wall of the reaction autoclave body, and the liquid nitrogen circulation refrigeration device and the thermometer are disposed on an outer wall of the reaction autoclave body;

the pressure control device is disposed on the reaction autoclave lid, the water level control device is disposed on an upper inner wall of the reaction autoclave body, and the conductivity testing device is disposed on an inner bottom of the reaction autoclave body.

12. The method according to claim 7, wherein the experimental apparatus further comprises a supercritical $CO_2$ circulation device, the supercritical $CO_2$ circulation device comprises a confining pressure pump, a circulation pump, a temperature controller, a temperature sensor, a heater, a cooler, and a natural cooler, the confining pressure pump is in communication with an interior of the reaction autoclave body, the confining pressure pump is provided with the temperature controller, and the confining pressure pump is further provided with two circulation pumps, the two circulation pumps are respectively connected to the heater and the cooler, a natural cooler is provided between the heater and the cooler, and the heater, the cooler, and the natural cooler are provided with temperature sensors.

13. The method according to claim 7, wherein the experimental apparatus further comprises a liquid defoaming device, the liquid defoaming device comprises a stirring rod and an ultrasonic defoamer, the stirring rod is disposed inside the reaction autoclave body for stirring a liquid inside the reaction autoclave body, and the ultrasonic defoamer is disposed inside the reaction autoclave body for eliminating bubbles inside the reaction autoclave body.

14. The method according to claim 7, wherein the experimental apparatus further comprises a data acquisition device, the data acquisition device comprises a filter, an outlet pressure sensor, a back pressure vessel, a back pressure pump, a gas-liquid separator, a beaker, a dryer, a flow pressure gauge, a gas chromatograph, and a data acquisition center, the filter is in communication with an interior of the reaction autoclave body, the outlet pressure sensor is disposed at a gas outlet of the filter, the filter is connected to the gas-liquid separator and the back pressure vessel respectively, the back pressure vessel is connected to the back pressure pump via the dryer, a liquid inside the filter enters the beaker through the gas-liquid separator, a gas inside the filter is analyzed and measured by the flow pressure gauge and the gas chromatograph after passing through the gas-liquid separator, the dryer is disposed between the gas-liquid separator and the flow pressure gauge, and the data acquisition center is configured to display measurement results of gas and liquid.

15. The method according to claim 7, wherein in the experimental apparatus, the reaction autoclave further comprises an explosion-proof glass observation window and a magnetic glass wiper, the explosion-proof glass observation window is embedded on the reaction autoclave body, the magnetic glass wiper is magnetically attached to the explosion-proof glass observation window, and the reaction autoclave body is further provided with an injection/extraction port for extracting and injecting gas or liquid.

16. The method for the shale supercritical synergistic penetration and imbibition based on the damping vibration according to claim 11, wherein in the step S5, a process of measuring the mass of the rock sample after immersion by the damping vibration measurement device is as follows:

the dual control switch connects the power source and the electromagnet, after the electromagnet is energized, the electromagnet pulls the magnetic rod down, driving the extendable sample clamp to move downwards, and the first spring is pulled downwards;

by adjusting a power supply voltage, a descending speed of the extendable sample clamp is observed until a bottom of the magnetic rod touches the pressure-sensitive sensor;

the pressure-sensitive sensor captures a pressure of the magnetic rod, triggers the dual control switch to disconnect a connection between the power source and the electromagnet, and connect the solenoid coil, the power source, and the ammeter;

based on the electromagnet being de-energized, under a restoring force of the first spring, the extendable sample clamp and the magnetic rod are pulled upwards, the magnetic rod oscillates up and down and continuously cuts the magnetic field lines within the solenoid coil;

based on the ammeter monitoring in real time the induced current generated by cutting the magnetic field lines, an electrical signal is captured, a vibration frequency of the magnetic rod is obtained, and the vibration frequency of the magnetic rod is combined with a gas pressure inside the reaction autoclave body, the mass of the rock sample after immersion is calculated.

17. The method for the shale supercritical synergistic penetration and imbibition based on the damping vibration according to claim 12, wherein in the step S5, a process of measuring the mass of the rock sample after immersion by the damping vibration measurement device is as follows:

the dual control switch connects the power source and the electromagnet, after the electromagnet is energized, the electromagnet pulls the magnetic rod down, driving the extendable sample clamp to move downwards, and the first spring is pulled downwards;

by adjusting a power supply voltage, a descending speed of the extendable sample clamp is observed until a bottom of the magnetic rod touches the pressure-sensitive sensor;

the pressure-sensitive sensor captures a pressure of the magnetic rod, triggers the dual control switch to disconnect a connection between the power source and the electromagnet, and connect the solenoid coil, the power source, and the ammeter;

based on the electromagnet being de-energized, under a restoring force of the first spring, the extendable sample clamp and the magnetic rod are pulled upwards, the magnetic rod oscillates up and down and continuously cuts the magnetic field lines within the solenoid coil;

based on the ammeter monitoring in real time the induced current generated by cutting the magnetic field lines, an electrical signal is captured, a vibration frequency of the magnetic rod is obtained, and the vibration frequency of the magnetic rod is combined with a gas pressure inside the reaction autoclave body, the mass of the rock sample after immersion is calculated.

18. The method for the shale supercritical synergistic penetration and imbibition based on the damping vibration according to claim 13, wherein in the step S5, a process of measuring the mass of the rock sample after immersion by the damping vibration measurement device is as follows:

the dual control switch connects the power source and the electromagnet, after the electromagnet is energized, the electromagnet pulls the magnetic rod down, driving the extendable sample clamp to move downwards, and the first spring is pulled downwards;

by adjusting a power supply voltage, a descending speed of the extendable sample clamp is observed until a bottom of the magnetic rod touches the pressure-sensitive sensor;

the pressure-sensitive sensor captures a pressure of the magnetic rod, triggers the dual control switch to disconnect a connection between the power source and the electromagnet, and connect the solenoid coil, the power source, and the ammeter;

based on the electromagnet being de-energized, under a restoring force of the first spring, the extendable sample clamp and the magnetic rod are pulled upwards, the magnetic rod oscillates up and down and continuously cuts the magnetic field lines within the solenoid coil;

based on the ammeter monitoring in real time the induced current generated by cutting the magnetic field lines, an electrical signal is captured, a vibration frequency of the magnetic rod is obtained, and the vibration frequency of the magnetic rod is combined with a gas pressure inside the reaction autoclave body, the mass of the rock sample after immersion is calculated.

19. The method for the shale supercritical synergistic penetration and imbibition based on the damping vibration according to claim 14, wherein in the step S5, a process of measuring the mass of the rock sample after immersion by the damping vibration measurement device is as follows:

the dual control switch connects the power source and the electromagnet, after the electromagnet is energized, the electromagnet pulls the magnetic rod down, driving the extendable sample clamp to move downwards, and the first spring is pulled downwards;

by adjusting a power supply voltage, a descending speed of the extendable sample clamp is observed until a bottom of the magnetic rod touches the pressure-sensitive sensor;

the pressure-sensitive sensor captures a pressure of the magnetic rod, triggers the dual control switch to disconnect a connection between the power source and the electromagnet, and connect the solenoid coil, the power source, and the ammeter;

based on the electromagnet being de-energized, under a restoring force of the first spring, the extendable sample clamp and the magnetic rod are pulled upwards, the magnetic rod oscillates up and down and continuously cuts the magnetic field lines within the solenoid coil;

based on the ammeter monitoring in real time the induced current generated by cutting the magnetic field lines, an electrical signal is captured, a vibration frequency of the magnetic rod is obtained, and the vibration frequency of the magnetic rod is combined with a gas pressure inside the reaction autoclave body, the mass of the rock sample after immersion is calculated.

20. The method for the shale supercritical synergistic penetration and imbibition based on the damping vibration according to claim 15, wherein in the step S5, a process of measuring the mass of the rock sample after immersion by the damping vibration measurement device is as follows:

the dual control switch connects the power source and the electromagnet, after the electromagnet is energized, the electromagnet pulls the magnetic rod down, driving the extendable sample clamp to move downwards, and the first spring is pulled downwards;

by adjusting a power supply voltage, a descending speed of the extendable sample clamp is observed until a bottom of the magnetic rod touches the pressure-sensitive sensor;

the pressure-sensitive sensor captures a pressure of the magnetic rod, triggers the dual control switch to disconnect a connection between the power source and the electromagnet, and connect the solenoid coil, the power source, and the ammeter;

based on the electromagnet being de-energized, under a restoring force of the first spring, the extendable sample clamp and the magnetic rod are pulled upwards, the magnetic rod oscillates up and down and continuously cuts the magnetic field lines within the solenoid coil;

based on the ammeter monitoring in real time the induced current generated by cutting the magnetic field lines, an electrical signal is captured, a vibration frequency of the magnetic rod is obtained, and the vibration frequency of the magnetic rod is combined with a gas pressure inside the reaction autoclave body, the mass of the rock sample after immersion is calculated.

\* \* \* \* \*